(12) United States Patent
Timken et al.

(10) Patent No.: US 6,747,182 B2
(45) Date of Patent: Jun. 8, 2004

(54) PRODUCTION OF ALKYLATED AROMATIC COMPOUNDS USING DEALUMINATED CATALYSTS

(75) Inventors: Hye Kyung C. Timken, Albany, CA (US); Arthur W. Chester, Cherry Hill, NJ (US); Susan Ardito, Ocean, NJ (US); Mark P. Hagemeister, Montville, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/813,170

(22) Filed: Mar. 20, 2001

(65) Prior Publication Data

US 2002/0049359 A1 Apr. 25, 2002

Related U.S. Application Data

(60) Provisional application No. 60/191,833, filed on Mar. 24, 2000.

(51) Int. Cl.[7] ................................................. C07C 2/66
(52) U.S. Cl. ........................................ 585/467; 585/455
(58) Field of Search ................................. 585/455, 467

(56) References Cited

U.S. PATENT DOCUMENTS

| | | | |
|---|---|---|---|
| 3,293,192 A | 12/1966 | Maher et al. ............... 252/430 |
| 3,449,070 A | 6/1969 | McDaniel et al. ............ 23/111 |
| 4,016,218 A | 4/1977 | Haag et al. ................ 260/671 |
| 4,211,665 A | 7/1980 | Pellegrini, Jr. .............. 252/63 |
| 4,238,343 A | 12/1980 | Pellegrini, Jr. ............... 585/24 |
| 4,301,316 A | 11/1981 | Young ....................... 585/455 |
| 4,503,023 A | 3/1985 | Breck et al. ................ 423/328 |
| 4,570,027 A | 2/1986 | Boucher et al. ............ 585/455 |
| 4,604,491 A | 8/1986 | Dressler et al. .............. 585/26 |
| 4,663,025 A | 5/1987 | Fu ............................ 208/120 |
| 4,714,794 A | 12/1987 | Yoshida et al. ............... 585/26 |
| 4,738,940 A | * 4/1988 | Dufresne et al. ............. 502/66 |
| 4,861,932 A | 8/1989 | Chen et al. .................. 585/412 |
| 4,891,465 A | * 1/1990 | Taniguchi et al. .......... 585/462 |
| 4,954,325 A | 9/1990 | Rubin et al. ................ 423/328 |
| 4,980,328 A | 12/1990 | Kukes et al. ................. 502/67 |
| 5,013,699 A | 5/1991 | Vassilakis et al. ............ 502/73 |
| 5,034,563 A | 7/1991 | Ashjian et al. .............. 585/455 |
| 5,177,280 A | * 1/1993 | Juguin et al. ............... 585/323 |
| 5,177,284 A | * 1/1993 | Le et al. ..................... 585/455 |
| 5,191,134 A | 3/1993 | Le ............................. 585/446 |
| 5,191,135 A | 3/1993 | Dywer et al. ................ 585/455 |
| 5,208,197 A | 5/1993 | Vassilakis et al. ............ 502/67 |
| 5,227,352 A | 7/1993 | Tsujii et al. .................. 502/65 |
| 5,457,254 A | 10/1995 | Ardito et al. ................ 585/455 |
| 5,629,463 A | 5/1997 | Ardito et al. ................ 585/455 |
| 5,646,082 A | 7/1997 | Tan-no et al. ................ 502/65 |
| 5,980,859 A | * 11/1999 | Gajda et al. ................ 423/713 |
| 6,171,474 B1 | 1/2001 | Kasztelan et al. ...... 208/111.01 |
| 6,174,429 B1 | 1/2001 | George-Marchal et al. ...... 208/111.01 |

FOREIGN PATENT DOCUMENTS

| | | |
|---|---|---|
| EP | 0432132 A1 | 6/1991 |
| WO | WO 90/06283 | 6/1990 |
| WO | WO 00/18707 | 4/2000 |

OTHER PUBLICATIONS

Frilette, et al, "Catalysis by Crystalline Aluminosilicates: Characterization of Intermediate Pore–Size Zeolites by the 'Constraint Index'," *J. Catalysis*, 67, 218–222 (1981).

Hölderich, et al., "Zeolites: Catalysts for Organic Syntheses," *Agnew. Chem. Int. Ed. Engl.*, 27, 226–246 (1988).

Breck, D.W., "Zeolite Molecular Sieves, Structural Chemistry and Use," John Wiley Publisher, N.Y. p. 94 (1974).

Lippmaa, et al, "Investigation of the Structure of Zeolites by Solid–State High–Resolution [29] Si NMR Spectroscopy," *J. Am. Chem. Soc.*, 103, pp. 4992–4996 (1981).

Kim, J.–H., et al, "Effect of SiO2/Al2O3 Ratio of H–Mordenite on the Isopropylation of Naphthalene with Propylene," *Microporous Materials* 5 (1995), pp. 113–121.

Reyniers, M.–F., et al, "Influence of Coke Formation on the Conversion of Hydrocarbons II. i–Butene on HY–Zeolites," *Applied Catalysis A: General* 202 (2000), pp. 65–80.

Vergani, D., et al, "Isopropylation of Biphenyl Over Dealuminated Mordenite," *Applied Catalysis A: General* 163 (1997), pp. 71–81.

Colon, G., et al, "Liquid–phase Alkylation of Naphthalene by Isopropanol Over Zeolites. Part 1: HY Zeolites," *Applied Catalysis A: General* 168 (1998), pp. 81–92.

Brzozowski, Robert, "Shape–selective Reactions of Naphthalene Over Zeolites," *Applied Catalysis A: General* 166 (1998), pp. 21–27.

\* cited by examiner

Primary Examiner—Thuan D Dang

(57) ABSTRACT

A process for preparing alkyl substituted aromatic compounds by alkylating an aromatic compound with an alkylating agent in the presence of a porous crystalline zeolite in which the zeolite has been selectively deluminated to remove nonframework aluminum.

20 Claims, No Drawings

PRODUCTION OF ALKYLATED AROMATIC COMPOUNDS USING DEALUMINATED CATALYSTS

This application claims priority to U.S. Provisional Application Serial No. 60/191,833, filed Mar. 24, 2000.

FIELD OF THE INVENTION

This invention relates to the production of alkylated aromatic compounds such as, for example, alkyl naphthalenes and substituted alkyl naphthalenes.

BACKGROUND OF THE INVENTION

Alkylaromatic fluids have been proposed for use as certain types of functional fluids where good thermal and oxidative properties are required. For example, U.S. Pat. No. 4,714,794 describes the monoalkylated naphthalenes as having excellent thermal and oxidative stability, low vapor pressure and flash point, good fluidity and high heat transfer capacity and other properties which render them suitable for use as thermal medium oils. The use of a mixture of monoalkylated and polyalkylated naphthalenes as a base for synthetic functional fluids is described in U.S. Pat. No. 4,604,491. U.S. Pat. Nos. 4,211,665 and 4,238,343 describe the use of alkylaromatics as transformer oils.

The alkylated naphthalenes are usually produced by the alkylation of naphthalene or a substituted naphthalene in the presence of an acidic alkylation catalyst such as a Friedel-Crafts catalyst, for example, an acidic clay as described in U.S. Pat. Nos. 4,714,794 or 4,604,491, or a Lewis acid such as aluminum trichloride as described in U.S. Pat. Nos. 4,211,665 and 4,238,343. The use of a collapsed silica-alumina zeolite for the catalytic alkylation of aromatic compounds such as naphthalene is disclosed in U.S. Pat. No. 4,570,027. The use of various zeolites including intermediate pore size zeolites such as ZSM-5 and large pore size zeolites such as zeolite L and ZSM-4 for the alkylation of various monocyclic aromatics such as benzene is disclosed in U.S. Pat. No. 4,301,316.

In the formulation of functional fluids based on the alkyl naphthalenes, it has been found that the preferred alkyl naphthalenes are the mono-substituted naphthalene since they provide the best combination of properties in the finished product. Because the mono-alkylated naphthalenes posses fewer benzylic hydrogens than the corresponding di-substituted or polysubstituted versions, they have better oxidative stability and therefore form better functional fluids and additives. In addition, the mono-substituted naphthalenes have a kinematic viscosity in the desirable range of about 5–8 cSt (at 100° C.) when working with alkyl substituents of about 14 to about 18 carbon atoms chain length. Although the mono-alkylated naphthalenes may be obtained in admixture with more highly alkylated naphthalenes using conventional Friedel-Crafts catalysts such as those mentioned above, or by the use of zeolites such as USY, the selectivity to the desired mono-alkylated naphthalenes is not as high as desired.

Several recent advances have been made in this area which improve the yields of the desired mono-alkylated naphthenes.

U.S. Pat. No. 5,034,563 to Ashjian et al., which is incorporated herein by reference in its entirety, teaches use of a zeolite containing a bulky cation. The use of, e.g., USY with cations having a radius of at least about 2.5 Angstroms increases selectivity for desired products. Taught as suitable were zeolites containing hydrated cations of metals of Group IA, divalent cations, especially of Group IIA, and cations of the Rare Earths. The patent had examples in which H+, NH4+, and Na+ were added to USY zeolite by a procedure involving forming a slurry of zeolite and liquid, 1 hour of stirring, decantation, and a repeat of the exchange procedure.

U.S. Pat. No. 5,177,284, which is incorporated herein by reference in its entirety, discusses the desirable properties of alkylated naphthalene fluids with higher alpha:beta ratios, including improved thermal and oxidative stability. Le et al. found that several parameters influenced the alpha:beta ratio of the alkylated naphthalene products, including steaming the zeolite, lowering the alkylation temperature, or the use of acid-treated clay. Steamed USY catalyst gave excellent results in the examples. The patentees also mentioned use of zeolites with reduced activity due to base exchange, alkaline earth ion exchange, and use of boron-zeolite beta.

U.S. Pat. No. 5,191,135, which is incorporated herein by reference in its entirety, discloses the effect of co-feeding water for this reaction when using a large pore zeolite catalyst, such as zeolite Y. Adding from 1–3 wt % water to the feed improved the alkylation reaction, a result attributed to suppression of zeolite acid site activity.

U.S. Pat. No. 5,191,134, which is incorporated herein by reference in its entirety, disclosed a similar alkylation process using MCM-41.

U.S. Pat. No. 5,457,254 to Ardito et al., which is incorporated herein by reference in its entirety, discloses a naphthalene alkylation process whereby the presence of both ammonium and protonic species increases selectivity for production of long chain mono-alkyl substituted naphthalenes.

The present inventors did additional work to see if they could further improve this alkylation process. They wanted to increase the efficiency of the reaction both in terms of conversion and yields.

The present inventors have discovered that an alkylation catalyst comprising a large pore zeolite which has been dealuminated to remove non-framework aluminum by selective ion exchange in acidic conditions, provides unexpectedly superior activity over a corresponding catalyst without the dealumination treatment. The inventors also discovered that the catalyst of the invention is effective in alkylation of other compounds containing two aromatic rings including, but not limited to, diphenyl oxide, diphenyl sulfide, diphenyl methane, and biphenyl.

SUMMARY OF THE INVENTION

Accordingly, the present invention provides a process for preparing alkyl substituted aromatic compounds, including long chain alkyl substituted aromatic compounds, which comprises alkylating an aromatic compound with an alkylating agent possessing an alkylating aliphatic group having at least six carbon atoms under alkylation reaction conditions in the presence of an alkylation catalyst comprising a porous crystalline zeolite which has been selectively dealuminated, under acidic conditions, to remove non-framework aluminum.

DETAILED DESCRIPTION

The starting materials for the production of the alkylated aromatic compounds include the aromatic compounds themselves. The term "aromatic compound" is understood by those of ordinary skill in the art to refer to any compound having at least one aromatic ring, such as, for example, benzene, pyridine, naphthalene. The aromatic compound may be unsubstituted or substituted with, by way of non-limiting example, halogen, alkyl, alkenyl, nitro, amino, amido, carboxyl, carboxamido, etc. Naphthalenes include naphthalene itself as well the substituted naphthalenes which may contain, for example, one or more short chain alkyl groups containing up to about eight carbon atoms, such as methyl, ethyl or propyl. Suitable alkyl-substituted naphthalenes include, for example, alpha-methylnaphthalene, dimethylnaphthalene and ethylnaphthalene. Naphthalene itself is preferred since the resulting mono-alkylated products have better thermal and oxidative stability than the more highly alkylated materials for the reasons set forth above.

Various other aromatic chemical compounds containing one or two aromatic rings in the structure can also be alkylated by this process. Such compounds include, but are not limited to, alkylbenzenes such as benzene, toluene, xylenes, ethyl benzene, methylethyl benzene, trimethyl benzene, and propyl benzene. Also included are other two-ring aromatic compounds such as, for example, diphenyl oxide, diphenyl sulfide, diphenyl methane, biphenyl, and alkyl-substituted derivative compounds.

The alkylating agents which are used to alkylate the naphthalene include, but are not limited to, any aliphatic or aromatic organic compound having one or more available alkylating aliphatic groups capable of alkylating the naphthalene. The alkylating group itself should have at least about 6 carbon atoms, preferably at least about 8, and still more preferably at least about 12 carbon atoms. For the production of functional fluids and additives, the alkyl groups on the alkyl-naphthalene preferably have from about 12 to about 30 carbon atoms, with particular preference to about 14 to about 18 carbon atoms. A preferred class of alkylating agents are the olefins with the requisite number of carbon atoms, for example, the hexenes, heptenes, octenes, nonenes, decenes, undecenes, dodecenes, tridecenes, tetradecenes, pentadecenes, hexadecenes, heptadecenes, and octadecenes. Mixtures of the olefins, e.g., mixtures of C12–C20 or C14–C18 olefins, are also useful. Branched alkylating agents, especially oligomerized olefins such as, for example, the trimers, tetramers, pentamers, etc., of light olefins including, but not limited to, ethylene, propylene, the butylenes, etc., are also useful. Other useful alkylating agents which may be used include alcohols (inclusive of monoalcohols, dialcohols, trialcohols, etc.) such as, for example, hexanols, heptanols, octanols, nonanols, decanols, undecanols, and dodecanols; and alkyl halides such as hexyl chlorides, octyl chlorides, dodecyl chlorides; and higher homologs.

The alkylation reaction between the naphthalene and the alkylating agent is carried out in the presence of a zeolite catalyst which contains a cation of certain specified radius. The molecular size of the alkylation products will require a relatively large pore size in the zeolite in order for the products to leave the zeolite, indicating the need for a relatively large pore size in the zeolite, which will also tend to reduce diffusion limitations with the long chain alkylating agents. The large pore size zeolites are the most useful zeolite catalysts for this purpose although the less highly constrained intermediate pore size zeolites may also be used, as discussed below. The large pore size zeolites include, but are not limited to, zeolites such as faujasite, the synthetic faujasites (zeolites X and Y), zeolite L, ZSM4, ZSM-18, ZSM-20, MCM-68, mordenite, and offretite, which are generally useful for this purpose are characterized by the presence of a 12-membered oxygen ring system in the molecular structure and by the existence of pores with a minimum dimension of at least 7.4 Å, as described by Frilette et al. in J. Catalysis 67, 218–222 (1981). See also Chen et al., "Shape-Selective Catalysis in Industrial Applications," (Chemical Industries, Vol. 36) Marcel Dekker Inc., New York 1989, ISBN 0-8247-7856-1; and Hoelderich et al., Agnew. Chem. Int. Ed. Engl. 27, 226–246 (1988), especially pp. 226–229. The large pore size zeolites may also be characterized by a "Constraint Index" of not more than about 2, in most cases not more than about 1. Zeolite beta, a zeolite having a structure characterized by twelve-membered pore openings, is included in this class of zeolites although under certain circumstances it has a Constraint Index approaching the upper limit of 2 which is characteristic of this class of zeolites. The method for determining Constraint Index is described in U.S. Pat. No. 4,016,218, together with values for typical zeolites and of the significance of the Index in U.S. Pat. No. 4,861,932, to which reference is made for a description of the test procedure and its interpretation.

Zeolites whose structure is that of a ten-membered oxygen ring, generally regarded as the intermediate pore size zeolites, may also be effective catalysts for this alkylation reaction if their structure is not too highly constrained. Thus, zeolites such as ZSM-12 (Constraint Index 2) may be effective catalysts for this reaction. The zeolite identified as MCM-22 is a useful catalyst for this reaction. MCM-22 is described in U.S. patent application Ser. No. 07/254524, filed Oct. 6, 1988, and also in International Patent Application PCT/US88/04251, to which reference is made for a description of this zeolite. Thus, zeolites having a CI up to about 3 will generally be useful catalysts, although the activity may be found to be dependent on the choice of alkylating agent, especially its chain length, a factor which imposes diffusion limitations upon the choice of zeolite. MCM-49 and MCM-56 are also useful catalysts according to the present invention.

A highly useful zeolite for the production of the monoalkylated naphthalenes is ultrastable Y, usually referred to as USY. When this material contains hydrated cations, it catalyses the alkylation in good yields with excellent selectivity. Zeolite USY is a material of commerce, available in large quantities as a catalyst for the cracking of petroleum. It is produced by the stabilization of zeolite Y by a procedure of repeated ammonium exchange and controlled steaming. Processes for the production of zeolite USY are described in U.S. Pat. Nos. 3,402,966, 3,923,192, and 3,449,070; see also Wojciechowski, "Catalytic Cracking, Catalysts, Chemistry and Kinetics," (Chemical Industries, Vol. 25), Marcel Dekker, New York, 1986, ISBN 0-8247-7503-8, to which reference is made for a description of zeolite USY, its preparation and properties.

It is preferred to use a small crystal Y zeolite, ranging from about 0.2 to about 0.4 microns, although materials ranging from about 0.6 to about 1.3 micron, which is more typical of Y zeolite crystals, may also be used.

The alkylation reaction conditions include a temperature ranging from about 100° C. to about 400° C. and a pressure of from about 0.2 to about 25 atmospheres and a weight hourly space velocity of from about 0.1 to about 10. The mole ratio of the alkylatable aromatic to alkylating agent ranges from about 0.1:1 to about 50:1.

EXAMPLE 1

Preparation of $H^+/NH_4^+$ USY Crystal Sample

A commercial Na-form USY with a silica-to-alumina ratio of 5.5 and a unit cell size of 24.54 Å was used for this catalyst preparation. The Na-form USY was ammonium exchanged twice with 1 M ammonium sulfate solution at a pH of about pH 5.5 and washed with deionized water (10 cc/g zeolite). Then the wet USY zeolite was dried in an oven at 120° C. overnight. The material was air-calcined (5 cc air/g zeolite/min) for 3 hours at 350° C. to control the residual water and ammonia levels. The properties of USY are shown in Table 1.

EXAMPLE 2

A commercial Na-form USY with a silica-to alumina ratio of 5,5 and an unit cell size of 24.54 Å was used for this catalyst preparation. The Na-form USY was made a slurry with deionized (DI) water to target a 35 wt % solids level. A solution of 30 wt % ammonium sulfate was prepared, and then the pH was adjusted to 4.0 using 20 wt % $H_2SO_4$ solution. The pH 4.0 ammonium sulfate solution was added slowly to the USY slurry (1.3 g of 30% ammonium sulfate solution per 1 g zeolite) while the overall solution pH was adjusted to 4.0. The exchanged USY zeolite was filtered and washed with deionized water (10 cc/g zeolite) and then dried in an oven at 120° C. overnight. The material was air calcined (5 cc air/g zeolite/min) for 3 hours at 350° C. The properties of the final catalyst are shown in Table 1.

EXAMPLE 3

Preparation of Dealuminated H+/NH4+ USY Crystal Sample

The preparation procedure for this example is nearly identical to Example 2, except that the exchange pH was 3.5. The properties of the final catalyst are shown in Table 1.

EXAMPLE 4

Preparation of Dealuminated $H^+/NH_4^+$ USY Crystal Sample

The preparation procedure for this example is nearly identical to Examples 2 and 3, except that the exchange pH was 3.0 The properties of the final catalyst are shown in Table 1.

TABLE 1

Properties of $H^+/NH_4^+$ USY Crystal Samples

| Example No. | $Na^+$ USY Starting USY | $H^+/NH_4^+$ USY Example 1 | $H^+/NH_4^+$ USY Example 2 | $H^+/NH_4^+$ USY Example 3 | $H^+/NH_4^+$ USY Example 4 |
|---|---|---|---|---|---|
| Exchange pH for $NH_4^+$ Exchange | — | 5–6 | 4.0 | 3.5 | 3.0 |
| Calcination Temp ° C. | — | 350 | 350 | 350 | 350 |
| N, wt % | — | 0.67 | 0.37 | 0.70 | 0.63 |
| S, wt % | — | 0.30 | 0.1 | <0.06 | <0.06 |
| LOI, wt % | 95.7 | 92.0 | 92.8 | 91.3 | 82.7 |
| Surface area, $m^2/g$ | 808 | 829 | 740 | 808 | 861 |
| Na, wt % | 2.9 | 0.4 | 0.6 | 0.5 | 0.3 |
| $SiO_2$, wt % | 70.2 | 69.1 | 67.7 | 70.8 | 74.3 |
| $Al_2O_3$, wt % | 22.0 | 21.3 | 20.4 | 17.5 | 14.7 |
| Bulk $SiO_2/Al_2O_3$ Ratio (molar) | 5.4 | 5.5 | 5.6 | 6.9 | 8.6 |
| Unit Cell Size, Å, by XRD | 24.56, 24.54 | 24.54 | 24.54 | 24.52 | 24.48 |
| $SiO_2/Al_2O_3$ Ratio (molar) by XRD (a) | 7.0–7.6 | 7.6 | 7.6 | 8.1 | 9.6 |
| $SiO_2/Al_2O_3$ Ratio (molar) by NMR (b) | 8.8 | — | 8.8 | 9.1 | 9.7 |

(a): $SiO_2/Al_2O_3$ molar ratio calculated based on publication by D. W. Breck, "Zeolite Molecular Sieves, Structural Chemistry and Use," John Wiley Publisher, N.Y., p. 911 (1974). The Breck correlation was developed for $Na^+$ form USY. Application of the Breck correlation for the $Na^+$ $H^+/NH_4^+$ form USY may not give correct $SiO_2/Al_2O_3$ molar ratios, but the data clearly show a trend consistent with the $^{29}Si$ NMR results.
(b): $SiO_2/Al_2O_3$ molar ratio calculated from $^{29}Si$ NMR based on publication by E. Lippmaa, M. Maegi, A. Samoson, and G. Englehardt, J. Am. Chem. Soc., 103, p. 4992 (1981).

The results above show that an ammonium sulfate exchange at pH 3.5 or above removes some of the aluminum (Al) species in USY while the unit cell size is rather constant (varies only from 24.54 Å to 24.52 Å) The constant unit cell size means that the framework $SiO_2/Al_2O_3$ molar ratio, e.g., framework Al content, is rather constant. The results suggest that we are selectively removing the non-framework Al in USY during the ammonium exchange at pH 3.5. The ammonium exchange at pH 3.0 removes not only the non-framework Al but also some of the framework Al. The $SiO_2/Al_2O_3$ molar ratios determined by NMR also show that ammonium exchange at pH 3.5 selectively removes the non-fraework Al, and at pH 3.0 both framework and non-famework Al are removed.

The extent of dealumination can be estimated as follows. For example, if we subject 100 g of Na+-form USY (100% solids basis) to the exchanges in the above examples we can estimate the following yields of $Na_2O$ and $Al_2O_3$ assuming the $SiO_2$ content in USY stays constant during the exchange (this assumption is reasonable since $SiO_2$ does not dissolve in an acidic solution). The following estimates were made using the bulk $SiO_2/Al_2O_3$ molar ratios determined by elemental analysis and the framework $SiO_2/Al_2O_3$ molar ratios determined by $^{29}Si$ NMR.

TABLE 2

Estimates of Framework and Non-Framework Al Dealumination of $H^+/NH_4^+$ USY Crystal Samples

| | Exchange pH | | | |
|---|---|---|---|---|
| | Na USY Starting USY | pH 4 Exchange Example 1 | pH 3.5 Exchange Example 2 | pH 3.0 Exchange Example 3 |
| Total $SiO_2$, g | 73.8 | 73.8 | 73.8 | 73.8 |
| Total $Na_2O$, g | 3.1 | 0.6 | 0.5 | 0.3 |
| Total $Al_2O_3$, g | 23.1 | 22.2 | 18.2 | 14.6 |
| g $Al_2O_3$, from framework (a) | 14.7 | 14.7 | 14.3 | 13.7 |
| g $Al_2O_3$, from non-framework (b) | 8.4 | 7.5 | 3.9 | 0.9 |
| wt % dealumination from framework | base | 0% | 3% | 7% |
| wt % dealumination from non-framework | base | 11% | 54% | 89% |

(a): All weights are based on a 100 g starting Na-USY at 100% solids basis. Ammonium exchange will cause some loss of $Al_2O_3$ and $Na_2O$, thus the total will be less than 100 g for the exchanged samples.
(b): The framework Al content is calculated from $SiO_2/Al_2O_3$ molar ratio determined by $^{29}Si$ NMR based on publication by E. Lipmaa, M. Maeigi, A. Samoson, and G. Englehardt, J. Am. Chem. Soc., 103, 4992 (1981).
(c): The non-framework Al content is an estimate, a difference between the total $Al_2O_3$ content and the $Al_2O_3$ content corresponding to framework Al.

EXAMPLE 5

Catalytic evaluation of $H^+/NH_4^+$ USY Crystal Samples

Three H+/NH4+ USY samples from Examples 2 through 4 were evaluated for alkylating naphthalene with a long chain alpha olefin to produce alkylated naphthalene lube base stocks. The alkylation experiment was carried out in a stirred vessel using 3.7 wt % of catalyst and 96.3 wt % of 1.2:1 molar ratio of alpha C16 olefin:naphthalene. The reactants in the vessel were then heated to 200° C. and held at the temperature for 2 hours, under nitrogen atmosphere. The total liquid product was then analyzed using gas chromatography to determine the amounts of unreacted naphthalene, olefin, monoalkylate and dialkylate. The results are summarized in Table 3.

TABLE 3

Catalyst Performance vs. Dealumination of $H^+/NH_4^+$ USY Crystal Samples

| | Example 2 | Example 3 | Example 4 |
|---|---|---|---|
| Exchange pH | pH 4.0 | pH 3.5 | pH 3.0 |
| Naphthalene | 85.4 | 94.7 | 94.7 |

TABLE 3-continued

Catalyst Performance vs. Dealumination of $H^+/NH_4^+$ USY Crystal Samples

| | Example 2 | Example 3 | Example 4 |
|---|---|---|---|
| Conversion wt % | | | |
| Total Lube yield, wt % | 84.8 | 92.4 | 95.1 |
| Product Distrib., wt %, | 77.7 | 85.8 | 79.8 |
| Monoalkylated + Diolefins | | | |
| Dialkylated | 7.1 | 6.6 | 15.3 |
| Unreacted Naphthalene | 4.7 | 1.7 | 1.7 |
| Unreacted Olefins | 10.5 | 5.9 | 3.2 |

The results in Table 3 show that the exchange condition is one of the important variables in alkylated naphthalene catalyst performance. Ammonium sulfate exchange at pH 3.5 or below is preferred since it improves the naphthalene conversion by 9.3 wt % (85.4% to 94.7%) and the corresponding lube yield. It also lowers the content of unreacted starting materials at the end of the batch reaction, thus improving the recovery process of the unreacted reactants.

The catalyst performance of the above USY samples are related to dealumination of non-framework Al (so-called "junk Al") in USY as shown in Table 4. Ammonium exchange at pH 3.5 or below selectively removes the non-framework Al or other occluded debris in USY.

TABLE 4

Catalyst Performance vs. Dealumination of $H^+/NH_4^+$ USY Crystal Samples

| Exchange pH | Conversion, wt % @ 200° C. | wt % dealumination from framework Al | wt % dealumination from non-framework Al |
|---|---|---|---|
| Na USY | — | base | base |
| pH 4.0 exch | 85.4 | 0 | 11 |
| pH 3.5 exch | 94.7 | 3 | 54 |
| pH 3.0 exch | 94.7 | 7 | 89 |

The advantage we observed with dealuminated USY is probably due to elimination of occluded materials such as non-framework Al, trapped sulfates, and other debris. While not wishing to be bound by any theory, we believe that alkylation of naphthalene with a long chain alkyl olefin inside USY crystals is hindered significantly by diffusion of the bulky molecules in a liquid phase. By eliminating occluded materials inside USY, the diffusion might be improved. As a result, the reactivity is enhanced. This is consistent with our observation that removal of non-framework Al, not the framework Al, is critical to increase the catalyst activity.

EXAMPLE 6

Preparation and Evaluation of $[H^+/NH_4^+]$ USY/ Silica-Clay Spray Dried Catalysts Ammonium exchanged USYs prepared by procedures described in Examples 2 and 3 were used for these catalyst preparations (Examples 6-1 and 6-2, respectively).

Ammonium exchanged USY was slurried and ball milled for 16 hours to produce <5μ average particle size. A physical mixture of 40 parts milled USY slurry, 30 parts colloidal silica, and 30 parts kaolin clay was slurried to form a uniform mixture. All components were blended based on parts by weight on a 100% solids basis. Sufficient amount of deionized water was added to form a spray dryable mixture (approximately 32–34 wt % solids). The mixture was spray dried to fine spherical particles having a particle size of approximately 70μ. The spray product was then air calcined for 3 hours at 400° C. The properties of the final catalysts are shown in Table 5.

The [H+/NH4+] USY/Silica-Clay catalysts were evaluated for alkylation reaction under identical conditions as in Example 5, except that the catalyst charge was 5%. The process results are summarized in Table 5.

TABLE 5

Properties and Performances of [H+/NH4+] USY/Silica-Clay Catalysts Effect of Ammonium Exchange pH (5.0 wt % Catalyst Charge)

|  | Example 6-1 [H+/NH4+] USY/Silica-Clay | Example 6-2 [H+/NH4+] USY/Silica-Clay |
|---|---|---|
| Exchange pH | 4.0 | 3.5 |
| Calcination Temp., ° C. | 400 | 400 |
| N, wt % | 0.02 | 0.06 |
| S, wt % | 0.14 | 0.14 |
| LOI, wt % | 90.8 | 86.3 |
| Na, wt % | 0.4 | — |
| Surface Area, m²/g | — | 273 |
| Naphthalene Conv., wt % | 80.5 | 89.2 |
| Total Lube Yield, wt % | 82.5 | 83.4 |
| Product Distrib., wt % | | |
| Monoalkylated + Diolefins | 58.6 | 68.1 |
| Dialkylated | 23.9 | 15.3 |
| Unreacted Naphthalene | 6.3 | 3.5 |
| Unreacted Olefins | 11.2 | 13.5 |

Results in Table 5 again show that the exchange pH affects the final catalyst activity significantly. An ammonium sulfate exchange at pH 3.5 or below is preferred since it improves the naphthalene conversion by 8.7 wt % (80.5% to 89.2%) and the corresponding mono-alkylate yield.

EXAMPLE 7

Preparation and Evaluation of [H+/NH4+] USY/Silica-Clay Spray Dried Catalysts

NH4+-form USY, which was ammonium exchanged at pH 3.5 per procedures described in Example 3, was used for this catalyst preparation. The ammonium exchanged USY was slurried and ball milled for 16 hours to produce >5μ average particle size. A physical mixture of 75 parts milled USY slurry, 20 parts colloidal silica, and 5 parts kaolin clay was slurried to form a uniform mixture. All components were blended based on parts by weight on a 100% solids basis. Sufficient amount of deionized water was added to form a spray-dryable mixture (approximately 32–34 wt % solids). The mixture was spray dried to fine spherical particles with approximately 70μ average particle size. The spray product was then divided into three samples and air calcined for 3 hours at 125° C., 350° C., and 538° C., respectively. The properties of the final catalysts are shown in Table 6.

The above [H+/NH4+] USY/Silica-Clay catalysts were evaluated for alkylation reaction under identical conditions as in Example 6, except that the catalyst charge was 3.7 wt %. The process results are summarized in Table 6.

TABLE 6

Properties and Performances of [H+/NH4+] USY/Silica-Clay Catalysts Effect of Calcination Temperature (3.7 wt % Catalyst Charge)

|  | Example 7-2 [H+/NH4+] USY/Silica-Clay | Example 7-2 [H+/NH4+] USY/Silica-Clay | Example 7-3 [H+/NH4+] USY/Silica-Clay |
|---|---|---|---|
| Exchange pH | 3.5 | 3.5 | 3.5 |
| Calcination Temp., ° C. | 250 | 350 | 538 |
| N, wt % | 0.64 | 0.30 | 0.02 |
| S, wt % | 0.08 | 0.08 | 0.08 |
| Surface Area, m²/g | — | — | 478 |
| Naphthalene Conv., wt % | 91.0 | 94.4 | 93.8 |
| Total lube yield, wt % | 85.8 | 95.3 | 93.9 |
| Product Distrib., wt % | | | |
| Mono-alkylated + Olefins | 82.2 | 86.6 | 79.7 |
| Dialkylated | 3.6 | 8.7 | 14.2 |
| Unreacted naphthalene | 2.9 | 1.8 | 2.0 |
| Unreacted olefins | 11.3 | 2.9 | 4.1 |

This example shows that the catalyst activity and selectivity can be further varied by varying the H+ to NH4+ ratio of the [H+/NH4+] USY/Silica-Clay catalyst. By adjusting the calcination temperature, the residual N level was varied from about 0.64 wt % to about 0.02 wt %. As the catalyst contains more N, the catalyst tends to be less active and the selectivity toward monoalkylate reactant increases. These findings are consistent to the earlier results reported by Ardito et a. (2). The range of preferred N levels is similar to what Ardito et al. claimed earlier, wherein the ratio of ammonium to protonic species is within the range of 80:20 to 20:80 molar ratio.

EXAMPLE 8

Zeolite Loading Effect

Examples 5 and 6 contain catalysts with identical ingredients, but vastly different composition, particularly the zeolite content. As the zeolite content increases from about 40 wt % to about 75 wt %, the catalyst activity increases substantially. As shown in the table below, the catalyst activity comes mostly from USY in that the relative reactivity of the catalyst is proportional to the zeolite content.

|  | Example 5-2 40 wt % USY | Example 6-2 75 wt % USY |
|---|---|---|
| Catalyst Charge for Evaluation | 5 wt % | 3.7 wt % |
| Conversion @ 2 hrs. | 89.2% | 94.4% |
| USY Charge Ratio | 1.0 | 1.39 |
| Relative Reactivity | 1.0 | 1.43 |

The high-zeolite, high activity USY containing catalyst has an advantage in commercial practice. After each batch reaction, the catalyst needs to be filtered out and discarded. By lowering the total catalyst charge per batch reaction (from about 5 wt % to about 3–3.7 wt %), the filtration step would take much less time and the catalyst disposal will cost less.

EXAMPLE 9

Preparation and Evaluation of [H+/NH$_4$+] USY/Silica-Clay Catalyst Using High Unit Cell Size USY A commercial Na-form USY with a silica-to-alumina ratio of 5.5 and a unit cell size of 24.60 Å was used for this catalyst preparation. The Na-form USY was ammonium exchanged at pH 3.5 per procedures described in Example 3. The ammonium exchanged USY was slurried and ball milled for 16 hours to produce <5 average particle size. A physical mixture of 75 parts milled USY slurry, 20 parts colloidal silica, and 5 parts kaolin clay was slurried to form a uniform mixture. All components were blended based on parts by weight on a 100% solids basis. Sufficient amount of deionized water was added to form a spray dryable mixture (approximately 32–34 wt % solids). The mixture was spray dried to fine spherical particles with approximately 70$\mu$ average particle size. The spray product was then air calcined for 3 hours at 350° C. The properties of the final catalysts are shown in Table 7. The [H+/NH4+] USY/Silica-Clay catalyst was evaluated for alkylation reaction under identical conditions as in Example 6, except that the catalyst charge was about 3.0 wt %. The performance results were compared with a catalyst prepared per procedure in Example 7-2.

TABLE 7

Properties and Performance of [H+/NH$_4$+] USY/Silica-Clay Catalysts
Effect of Unit Cell Size of Starting USY (3.0 wt % Catalyst Charge)

|   | Example 9 [H+/NH$_4$+] USY/Silica-Clay | Example 6-2 [H+/NH$_4$+] USY/Silica-Clay |
| --- | --- | --- |
| Na-USY Unit Cell Size, Å | 24.60 | 24.54 |
| Calcination Temp., ° C. | 350 | 350 |
| N, wt % | 0.34 | 0.65 |
| S, wt % | 0.11 | 0.07 |
| LOI, wt % | 81.0 | 94.9 |
| Na, wt % | 0.5 | 0.6 |
| Surface Area, m$^2$/g | 573 | 529 |
| Naphthalene Conv. @ 2 hrs, wt % | 93.4 | 88.2 |
| Totat lube yield, wt % | — | 87.2 |
| Product Distrib., wt % | | |
| Monoalkylated + Diolefins | — | 78.4 |
| Di-alkylated | 8.4 | 8.8 |
| Unreacted naphthalene | 2.1 | 3.8 |
| Unreacted olefins | — | 9.0 |

The above example shows that the catalyst activity and selectivity can be varied by varying the unit cell size of the starting Na-USY crystals. By using larger unit cell size USY crystals, we were able to increase the catalyst activity even further. This effect of unit cell size to the catalyst performance for alkylated naphthalene synthesis was not been observed by others before.

EXAMPLE 10

Preparation of Alkyl Diphenyl Sulfides Using H+/NH$_4$+ USY Catalyst

The H+/NH4+ USY catalyst from Example 3 was evaluated for alkylation of diphenyl sulfide with a long chain alpha olefin to produce alkylated diphenyl sulfide lube base stock. 1-Hexadecene (224 g), diphenyl sulfide (186 g) and the H+/NH4+ USY catalyst (13.4 g) were added to a reaction flask and heated to 220° C. under a nitrogen atmosphere. After five hours, the reaction mass was cooled and the catalyst removed by filtering through a bed of diatomaceous earth filter medium (Celite 545). The filtrate was then heated to 196° C. and unreacted material (68.2 g) was removed through distillation at 4-mm Hg absolute pressure. The final product contains 94% monoalkylate and 6% dialkylate and had the following physical properties:

| 40C KV, cst | 27.27 |
| --- | --- |
| 100C KV, cSt | 4.871 |
| Viscosity Index | 100 |
| Pour Point, ° C. | −42 |

The alkylated product exhibits favorable VI and pour point suggesting the material could be useful as functional fluid or additive for synthetic lube stock.

EXAMPLE 11

Preparation of Alkyl Diphenyl Oxides Using [H+/NH$_4$+] USY/Silica-Alumina-Clay Catalyst A [H+/NH4+] USY/ Silica-Alumina-Clay catalyst was prepared per following procedure. USY with a silica-to-alumina ratio of 5.5 and a unit cell size of 24.54 Å was ammonium exchanged at pH 3.2. The ammonium exchanged USY was slurried and ball milled for 16 hours to produce <5 $\mu$ average particle size. A physical mixture of 75 parts milled USY slurry, 16.7 parts colloidal silica, 3.3 parts formic acid peptized alumina, and 5 parts kaolin clay was slurried to form a uniform mixture. All components were blended based on parts by weight on a 100% solids basis. Sufficient amount of deionized water was added to form a spray dryable mixture (approximately 32–34 wt % solids). The mixture was spray dried to fine spherical particles with approximately 70 $\mu$ average particle size. The spray product was then air calcined for 3 hours at 350° C.

The above catalyst was evaluated for alkylation of diphenyl oxide with a long chain alpha olefin to produce alkylated diphenyl oxide lube base stock. Diphenyl oxide (425 g), activated carbon (3.81 g) and the catalyst (19.0 g) were added to a reaction flask and heated to 200° C. under a nitrogen atmosphere. 1-Hexadecene (336 g) was added dropwise to the flask over two hours. After holding an additional 40 minutes, the reaction mass was cooled and the catalyst removed by filtering through a bed of diatomaceous earth filter medium (Celite 545). The filtrate was then heated to 240° C. and unreacted material was removed through distillation at 10-mm Hg absolute pressure. The final product (558 g) contained 97% monoalkylate and 3% dialkylate and had the following physical properties:

| 40C KV, cst | 23.29 |
| --- | --- |
| 100C KV, cSt | 4.361 |
| Viscosity Index | 90 |
| Pour Point, ° C. | −45 |

The alkylated product exhibits favorable VI and pour point suggesting the material could be useful as functional fluid or additive for synthetic lube stock.

EXAMPLE 12

Preparation of Alkyl Biphenyls Using H+/NH$_4$+ USY Catalyst

The H+/NH4+ USY catalyst from Example 3 was evaluated for alkylation of biphenyl with a long chain alpha olefin to produce alkylated biphenyl lube base stock. 1-Hexadecene (224 g), biphenyl (154 g) and the H+/NH4+ USY catalyst (19.9 g) were added to a reaction flask and heated to 140° C. under a nitrogen atmosphere. After five hours, 81% of the reactants had been converted to alkylates and the reaction mass was cooled and the catalyst removed by filtering through a bed of diatomaceous earth filter medium (Celite 545). The filtrate was then heated to 192° C. and unreacted material was removed through distillation at 4-mm Hg absolute pressure. The final product contains 96% monoalkylate and 4% dialkylate and had the following physical properties:

| | |
|---|---|
| 40C KV, cst | 32.17 |
| 100C KV, cSt | 5.157 |
| Viscosity Index | 83 |
| Pour Point, ° C. | −45 |

The alkylated product exhibits favorable VI and pour point suggesting the material could be useful as functional fluid or additive for synthetic lube stock.

EXAMPLE 13

Preparation of Alkyl Diphenylmethanes Using $H^+/NH_4^+$ USY Catalyst

The H+/NH4+ USY catalyst from Example 3 was evaluated for alkylation of diphenylmethane with a long chain alpha olefin to produce alkylated diphenylmethane lube base stock. 1-Hexadecene (224 g), diphenylmethane (168 g) and the H+/NH4+ USY catalyst (20.7 g) were added to a reaction flask and heated to 200°C. under a nitrogen atmosphere. After five hours, 92% of the reactants had been converted to alkylates and the reaction mass was cooled and the catalyst removed by filtering through a bed of diatomaceous earth filter medium (Celite 545). The filtrate was then heated to 184° C. and unreacted material was removed through distillation at 4-mm Hg absolute pressure. The final product contains 95% monoalkylate and 5% dialkylate and had the following physical properties:

| | |
|---|---|
| 40C KV, cst | 21.47 |
| 100C KV, cSt | 4.383 |
| Viscosity Index | 113 |
| Pour Point, ° C. | −48 |

The alkylated product exhibits favorable VI and pour point suggesting the material could be useful as functional fluid or additive for synthetic lube stock.

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

What is claimed is:

1. A process for preparing a long chain alkyl-substituted aromatic compound, comprising alkylating an aromatic compound with an alkylating agent possessing an alkylating aliphatic group having at least six carbon atoms under alkylation reaction conditions in the presence of an alkylation catalyst comprising USY zeolite, wherein the USY zeolite has been selectively dealuminated at a pH ranging from about 3 to about 6 to remove greater than about 50 wt % of non-framework aluminum and less than about 10 wt % of framework aluminum to form an alkylated aromatic compound possessing at least one alkyl group derived from the alkylating agent.

2. The process of claim 1, wherein the alkylating aliphatic group contains at least about 8 carbon atoms.

3. The process of claim 2, wherein the alkylating aliphatic group contains about 12 to about 30 carbon atoms.

4. The process of claim 1, wherein the alkylating agent comprises an olefin.

5. The process of claim 1, wherein the alkylation reaction conditions include a temperature ranging from about 100° C. to about 400° C., pressure of about 0.2 to about 25 atmospheres, a weight hourly space velocity of about 0.1 to about 10, and an alkylatable aromatic:alkylating agent mole ratio of about 0.1:1 to about 50:1.

6. The process of claim 1, wherein the porous crystalline zeolite comprises cations.

7. The process of claim 6, wherein the cations are selected from the group consisting of H+, NH4+, Na+, K+, Mg2+, Ca2+, Rare Earth ions, a mixture thereof.

8. The process of claim 1, wherein the non-framework aluminum is removed from the porous crystalline zeolite by ammonium exchange.

9. The process of claim 8, wherein the ammonium exchange is performed at a pH ranging from about 3.5 to about 6.0.

10. The process according to claim 8, wherein the ammonium exchange is performed at a pH ranging from about 3 to about 5.

11. The process according to claim 8, wherein the ammonium exchange is performed at a pH ranging from about 3.5 to about 6.

12. The process of claim 1, wherein the non-framework aluminum is removed from the porous crystalline zeolite by acid exchange.

13. The process of claim 12, wherein the acid exchange is performed with at least one organic acid.

14. The process of claim 12, wherein the acid exchange is performed with at least one inorganic acid.

15. The process according to claim 1, wherein the bulk $SiO_2/Al_2O_3$ ratio of the dealuminated USY zeolite ranges from about 5 to about 12.

16. The process according to claim 1, wherein the aromatic compound is naphthalene.

17. The process according to claim 1, wherein the aromatic compound is diphenyl oxide.

18. The process according to claim 1, wherein the organic material aromatic compound is diphenyl sulfide.

19. The process according to claim 1, wherein the organic material aromatic compound is diphenyl.

20. The process according to claim 1, wherein the organic material is diphenylmethane.

* * * * *